United States Patent [19]

Chin et al.

[11] Patent Number: 4,998,972

[45] Date of Patent: Mar. 12, 1991

[54] REAL TIME ANGIOSCOPY IMAGING SYSTEM

[75] Inventors: Albert K. Chin, Palo Alto; Anthony A. Nobles, Carson; Kwok Y. Lai, Los Angeles, all of Calif.

[73] Assignee: Thomas J. Fogarty, Palo Alto, Calif.

[21] Appl. No.: 328,760

[22] Filed: Mar. 23, 1989

Related U.S. Application Data

[63] Continuation of Ser. No. 187,591, Apr. 28, 1988, abandoned.

[51] Int. Cl.⁵ .............................................. A61B 1/06
[52] U.S. Cl. .................................. 128/6; 358/98; 128/666
[58] Field of Search ............... 128/4, 6, 7, 666, 668, 128/634; 604/53, 95; 358/98

[56] References Cited

U.S. PATENT DOCUMENTS

| 4,175,545 | 11/1979 | Termanini | 128/6 |
|---|---|---|---|
| 4,576,145 | 3/1986 | Tsuno et al. | 128/6 |
| 4,576,146 | 3/1986 | Kawazoe et al. | 128/6 |
| 4,619,247 | 10/1986 | Inoue et al. | 128/6 |
| 4,712,133 | 12/1987 | Kikuchi | 358/98 |
| 4,755,873 | 7/1988 | Kobayashi | 128/6 |
| 4,759,348 | 7/1988 | Cawood | 128/6 |
| 4,759,349 | 7/1988 | Betz et al. | 128/6 |
| 4,768,089 | 8/1988 | Kato | 128/6 |
| 4,827,907 | 5/1989 | Tashiro | 128/6 |

*Primary Examiner*—Edward M. Coven
*Assistant Examiner*—Jessica J. Harrison
*Attorney, Agent, or Firm*—Limbach, Limbach & Sutton

[57] ABSTRACT

An angioscopy imaging system which operates under the control of a computer system includes an optical scanning system which is inserted into a vessel, such as an artery, for generation of an image. An irrigation system provides pulsatile introduction of flush solution to the vessel to create clear a viewing field within the vessel for the optical scanning system. The computer system controls both the optical scanning system and the irrigation system such that the generation of the image is synchronized with the pulsatile introduction of the flush solution.

26 Claims, 11 Drawing Sheets

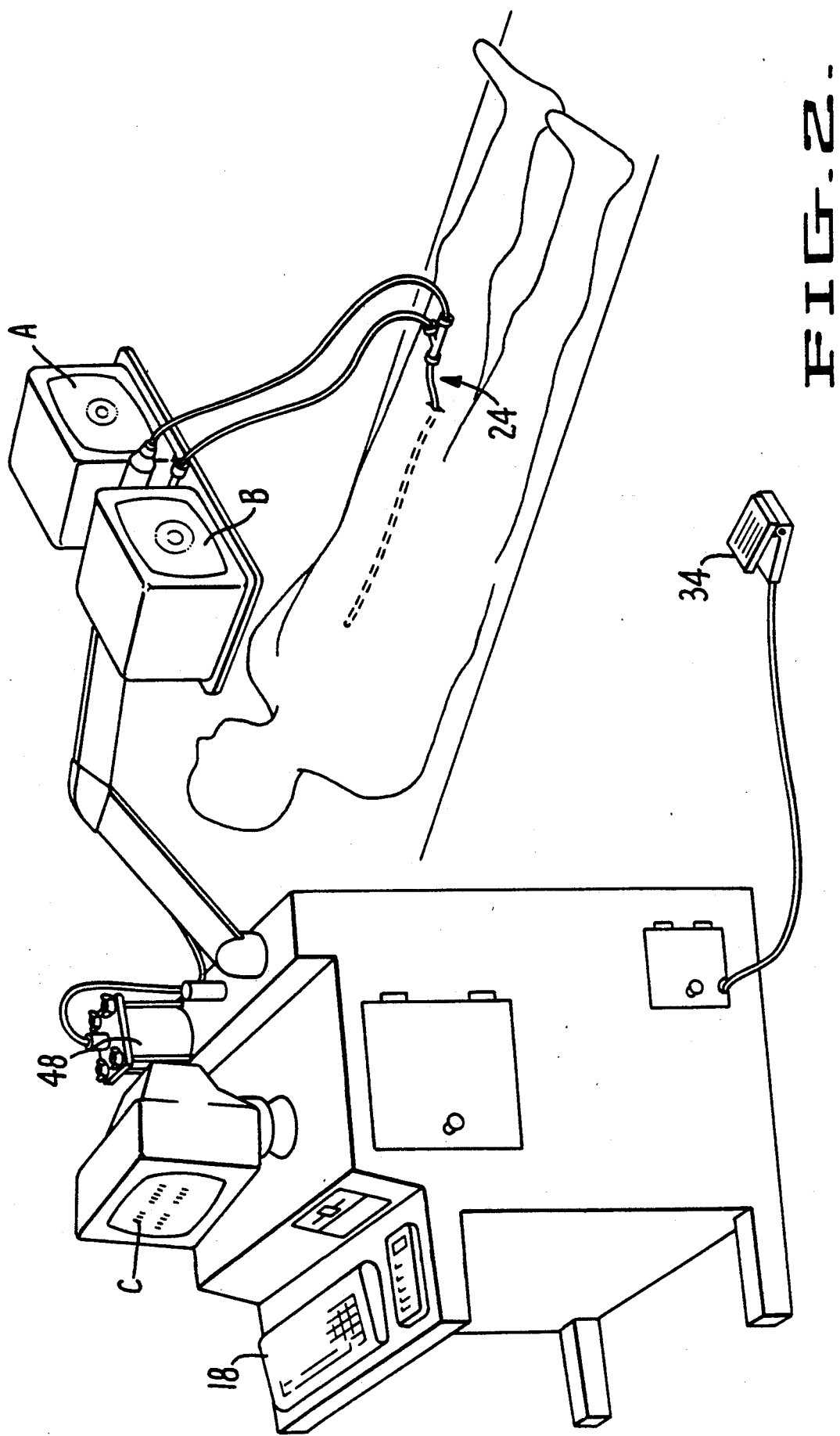

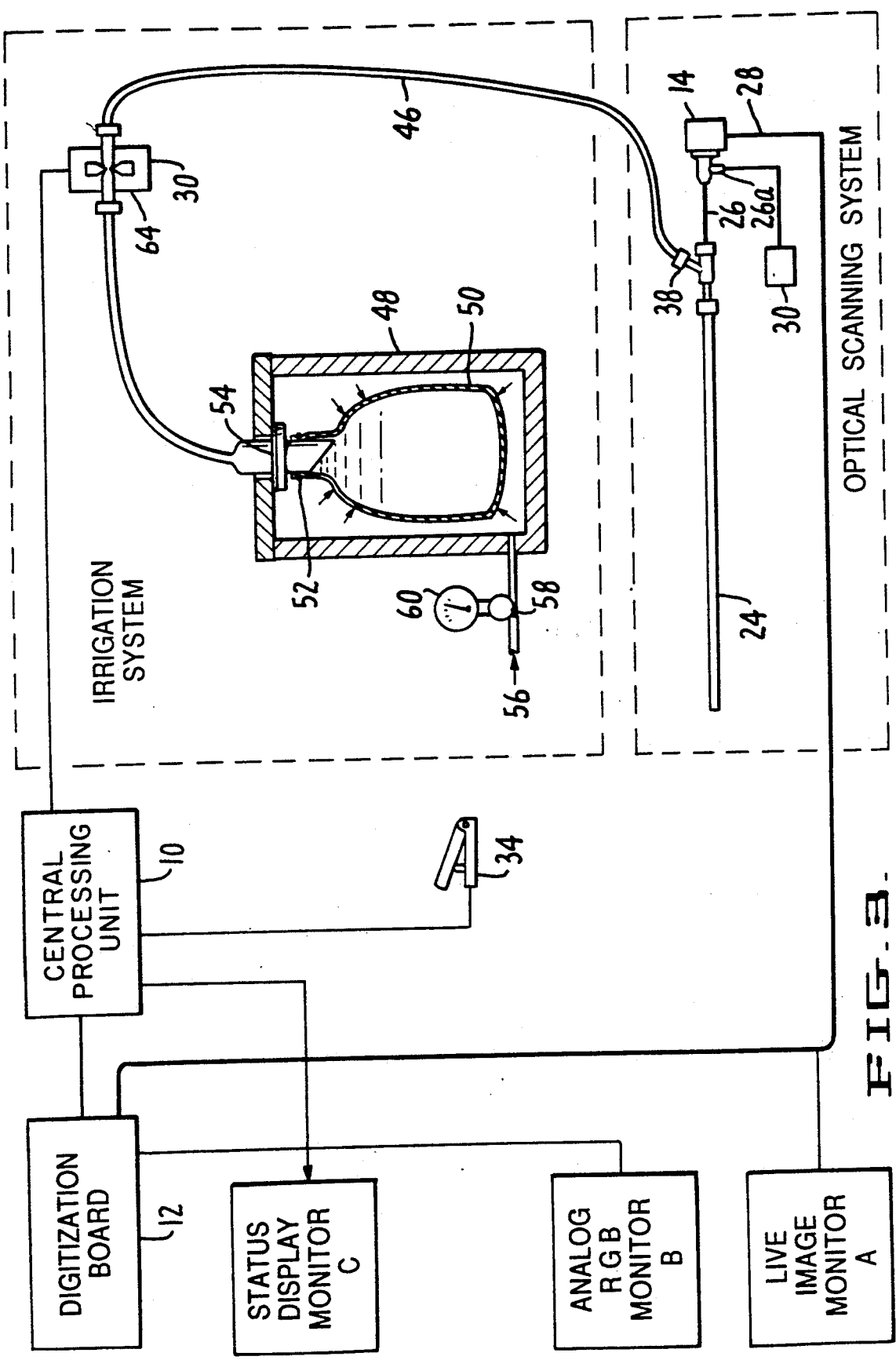

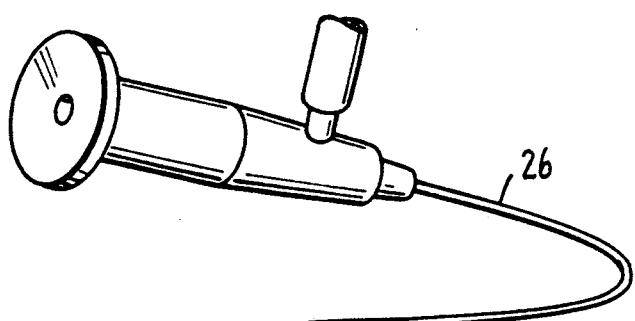
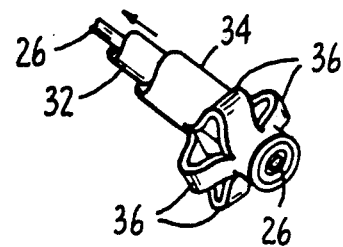
FIG.4B
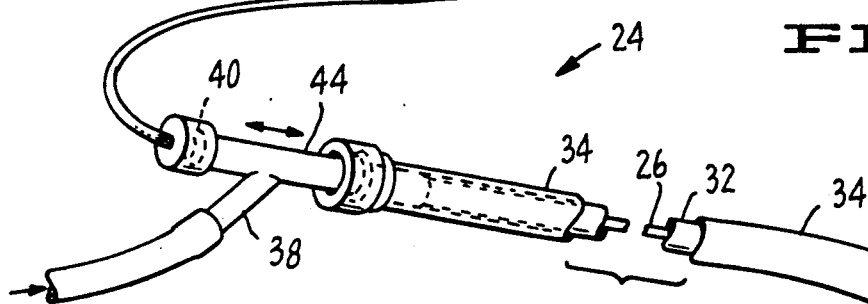
FIG.4A
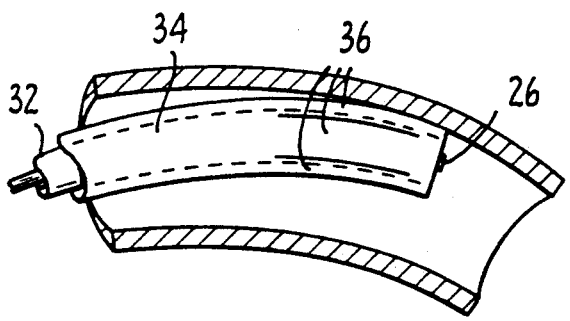
FIG.4C
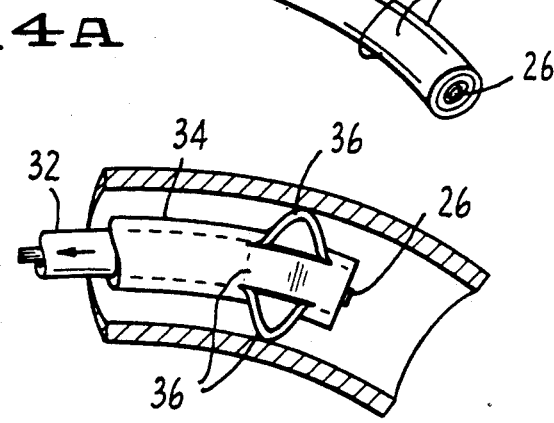
FIG.4D
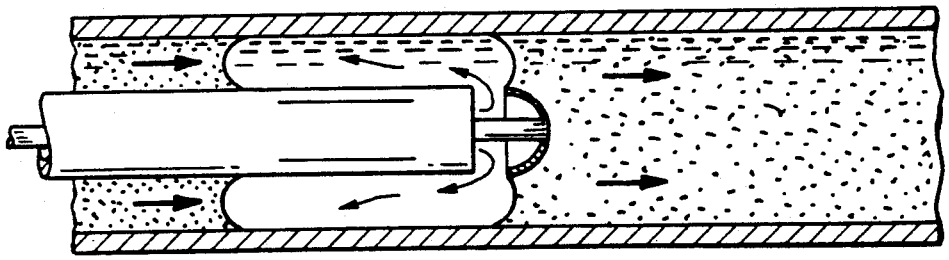
FIG.8A
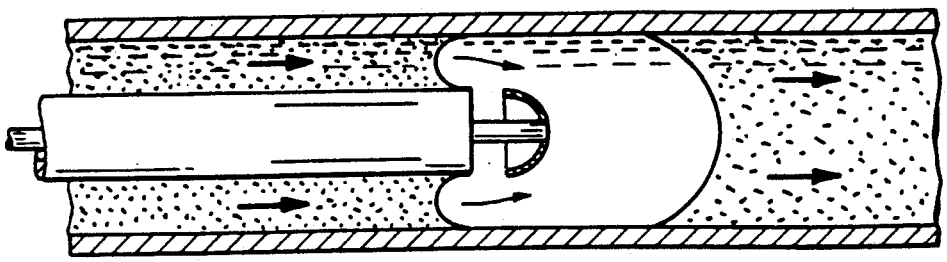
FIG.8B

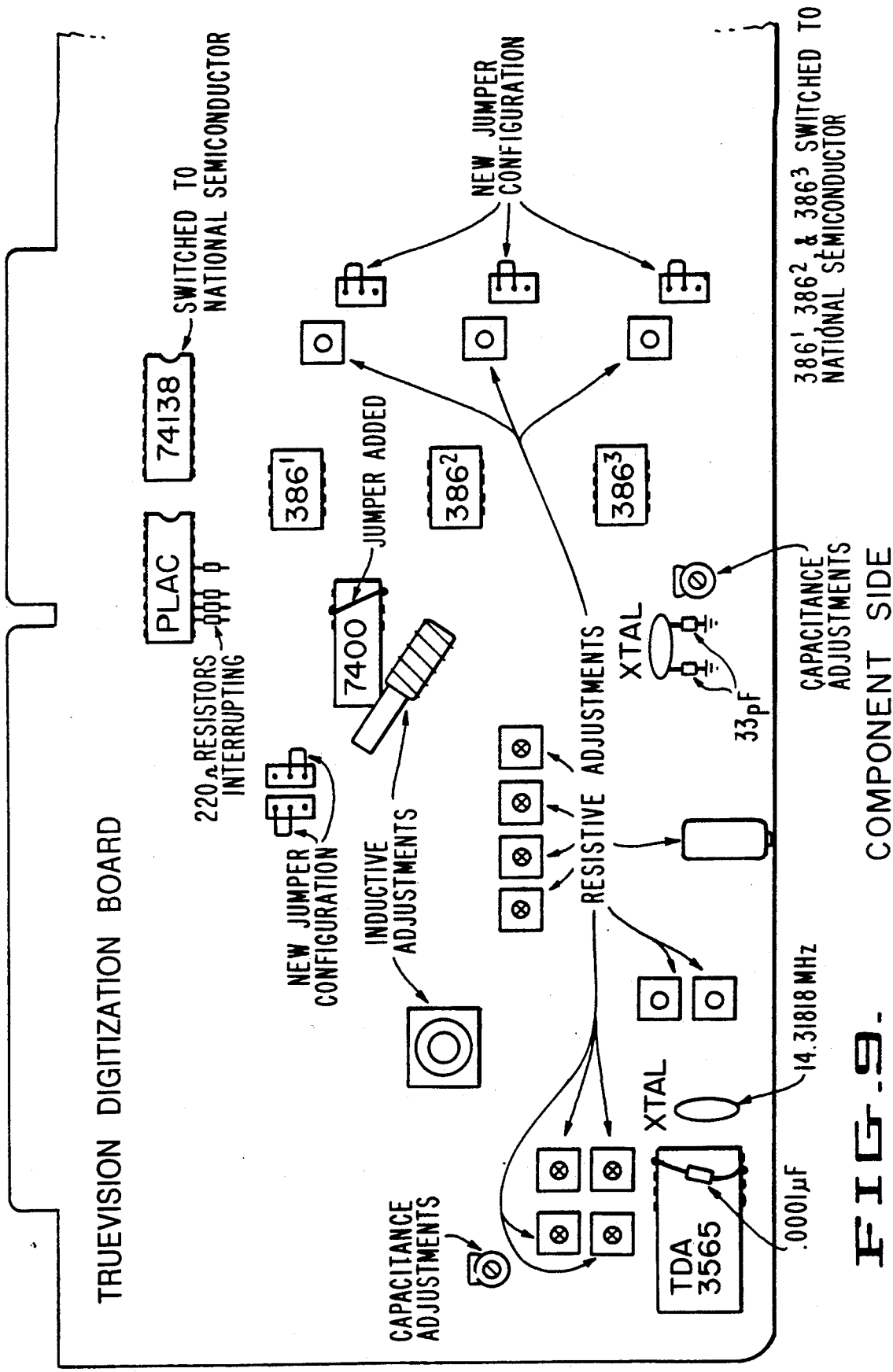

REAL TIME ANGIOSCOPY IMAGING SYSTEM

This is a continuation of co-pending application Ser. No. 187,591 filed on Apr. 28, 1988, now abandoned.

BACKGROUND OF THE INVENTION

1. Field of the Invention

The present invention relates to apparatus for direct visualization of body passages and, in particular, to an automated angioscopy imaging system that provides pulsatile irrigation coupled with synchronous real time imaging.

2. Discussion of the Prior Art

It is well-known that optical scopes may be used for direct visualization of body passages. For example, endoscopes are used for viewing the gastrointestinal tract, bronchoscopes are used for viewing bronchial passages, and arthroscopes are used for joint examination. These scopes are moved to a position within the body that the viewer desires to examine. The body passage is then visualized directly through the eyepiece of the scope or a video camera is attached to the scope to display the image on a video monitor.

An angioscope is used for viewing both the arterial and the venous systems. In the angioscopy procedure, a fiberoptic scope is inserted into the vessel through an incision and then threaded through the vessel to provide visualization at selected points along the length of the vessel. Sterile saline flush solution is introduced continuously into the vessel to provide a clear visualization field.

Angioscopy is a particularly difficult procedure in the arterial system. The pressure and the flow rate of the blood are much higher in the arteries than in the veins, making it difficult to obtain the clear, bloodless field required for the desired quality of visualization. If only a small amount of saline is used to flush away the blood, this flush is washed away too quickly to allow adequate visualization. On the other hand, if a larger amount of flushing solution is used, over a time period sufficient to allow adequate visualization, complications will arise. First, fluid overload of the patient will occur, causing electrolyte imbalance or congestive heart failure. Second, there will be a lack of perfusion to the tissue supplied by the artery undergoing angioscopy because the flushing fluid has cleared away the oxygen-carrying blood. This problem is particularly difficult in angioscopic evaluation of the coronary arteries, since the cardiac muscle cannot tolerate prolonged ischemia. Balloon occlusion may be used, but it too may cause ischemia.

Therefore, it would be highly desirable to have available an angioscopy system that provides clear visualization within the irrigation constraints described above.

SUMMARY OF THE INVENTION

An angioscopy imaging system in accordance with the present invention utilizes controlled saline irrigation to clear the viewing field and a synchronized, high-resolution imaging system to capture a high quality digitized image and hold it for viewing in real time. During the irrigation cycle, the angioscope image is projected directly on a video monitor. The image is saved on the monitor during the flush-interrupted cycle and then updated with the next active flush cycle.

This technique allows constant visualization of the artery, with second-by-second evaluation of the catheter position within the artery. It provides a real-time image of the artery, while allowing blood flow to occur over a large proportion of time. This decreases the danger of incurring ischemia during visualization.

An angioscopy imaging system in accordance with the present invention utilizes a catheter which houses the angioscope and provides a flushing channel which allows irrigation at the distal end of the angioscope. The saline flush creates a bolus which is visually clear over the focal distance of the angioscope. The pulses of pressurized saline are delivered on command from a computer system. The computer may be programmed to deliver a sequence of timed irrigations, or a single pulse may be delivered by means of a foot pedal switch connected to the computer.

Both the fiber optic angioscope and the irrigation catheter are placed inside a narrow blood channel and, immediately, a digitized picture is generated by a digitizer board and displayed on a monitor in real time. The main function of the computer is to allow the user to predefine the duration of the period during which saline solution is injected into the blood channel, thus clearing the viewing end of the angioscope and its surrounding. While the solution is being injected, a continuous live picture is also being generated on a separate monitor. At the end of the irrigation period, saline injection stops and the computer commands a freeze procedure, thus preserving the last image on the live monitor. The digitized image is periodically refreshed until a new, updated image is displayed in conjunction with the subsequent flush cycle.

The system program provides the user with absolute freedom in determining the length of the irrigation period to yield the best possible display, but with certain limitations so that it will not jeopardize the overall operation. The high speed digitizer allows for sufficiently short irrigation periods so that images are provided to the viewer in real time. With the image being frozen in time, any image processing functions can then be performed, such as save, zoom, change colors, move around and many others.

The system design utilizes state-of-the-art image processing and fiber optic camera technology. As stated above, the computer system controls all of the timing functions of the system and captures images for instantaneous, uninterrupted viewing. Each of the images can be individually processed or stored as a single picture to be called up for later display or to be printed as a slide for later presentation.

A better understanding of the features and advantages of the present invention will be obtained by reference to the following detailed description of the invention and accompanying drawings which set forth an illustrative embodiment in which the principles of the invention are utilized.

BRIEF DESCRIPTION OF THE DRAWINGS

FIG. 2 is a pictorial illustration of an angioscopy imaging system in accordance with the present invention in an operating room environment.

FIG. 3 is a schematic diagram illustrating an angioscope catheter and irrigation system for an angioscopy imaging system in accordance with the present invention.

FIG. 4A is a pictorial view illustrating an angioscope centering catheter utilized in accordance with a preferred embodiment of the present invention.

FIG. 4B is a pictorial view illustrating the distal end of the angioscope centering catheter shown in FIG. 1 after splaying of the longitudinal slitted sections.

FIG. 4C is a cross-sectional view illustrating the catheter shown in FIG. 4A in a curved section of vessel prior to centering.

FIG. 4D is a cross-sectional view illustrating the catheter shown in FIG. 4A in a curved section of vessel after centering.

FIGS. 8A and 8B are cross-sectional views illustrating introduction of flush solution utilizing a deflector shield.

FIG. 9 is a schematic diagram illustrating a Truevision digitization board which has been altered as shown for application in accordance with the present invention.

DETAILED DESCRIPTION OF THE INVENTION

Figure 1:
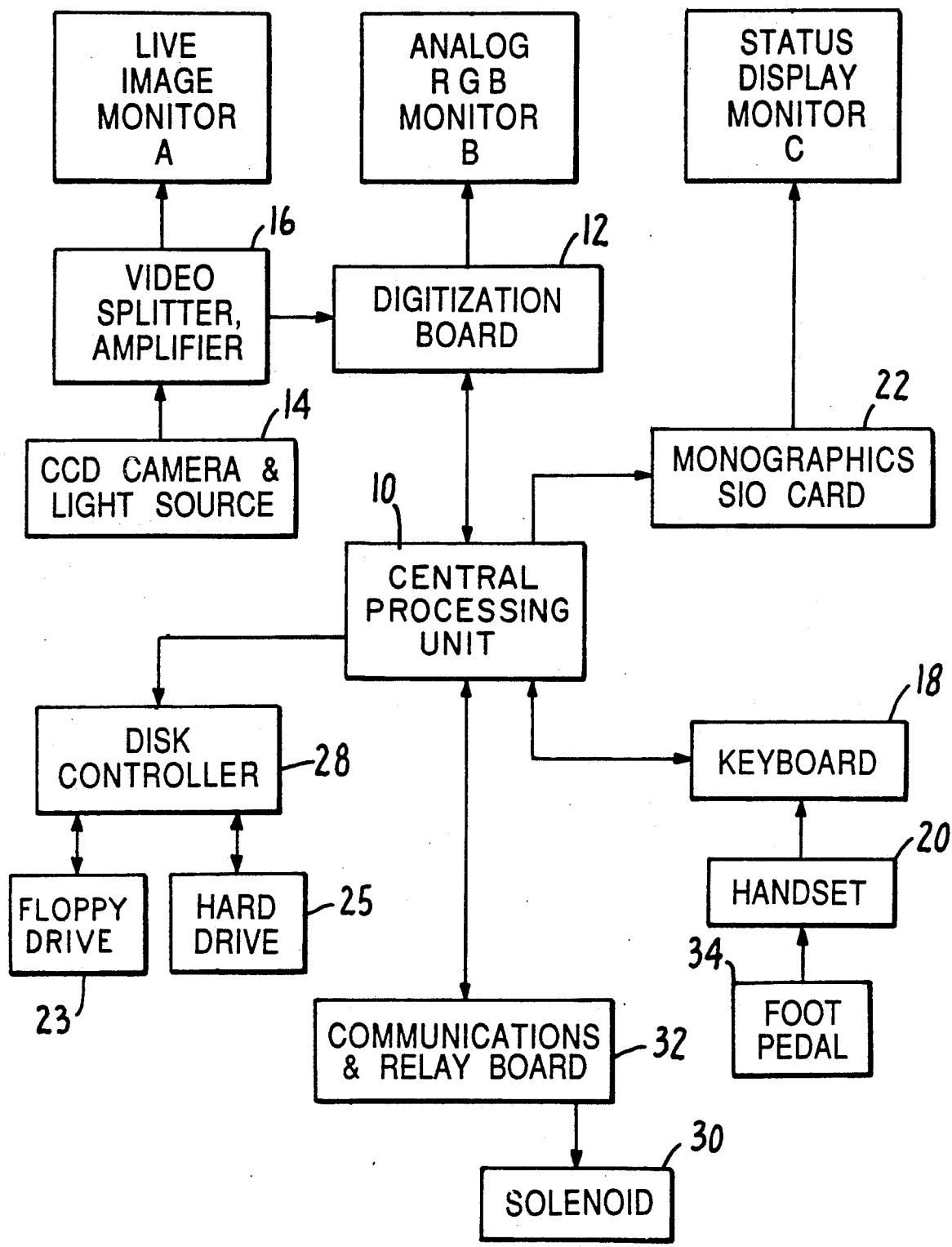
FIG. 1 is a block diagram illustrating the general concept of an angioscopy imaging system in accordance with the present invention.

An angioscopy imaging system in accordance with the present invention is illustrated in FIGS. 1-3, wherein like reference numerals specify like elements.

FIG. 1 provides an illustration of an angioscopy imaging system in accordance with the general concept of the present invention. The system operates under the control of a computer system which includes imaging control and irrigation control hardware. The imaging control hardware controls an optical scanning system, to be described in detail below, which is inserted into the interior of a vessel for generation of a digitized image. The irrigation control hardware controls an irrigation system, to be described in detail below, which provides pulsed introduction of flush solution into the interior of the artery to create a clear viewing field within the vessel for the optical scanning system. The computer system controls both the optical scanning system and the irrigation system such that the generation of the digitized image is synchronized with the pulsed introduction of the flush solution.

The system shown in FIG. 1 operates under the control of a central processing unit 10. The central processing unit 10 communicates with a digitization board 12 which generates a digitized image signal that corresponds to a live image captured by camera and light source 14, as described in detail below. The live image signal generated by camera/light source 14 is provided to the digitization board 12 via a video splitter/amplifier 16 which also provides the live image signal to monitor A for direct display. The digitization board 12 provides the digitized image signal to monitor B for display of a digital image. Status information, which can be entered either via a keyboard 18 or a handset 20, is displayed on a status display monitor C via monographic serial input/output card 22. CPU 10 can access both floppy drive storage 23 and hard drive storage 25 via a disk controller 28. As will be described in detail below, pulses of pressurized saline flush solution are provided to an angioscope catheter on command from the central processing unit 10 which opens and closes a solenoid valve 30 via communications and relay board 32.

A pictorial illustration of an angioscopy imaging system in accordance with the present invention in an operating room environment is provided in FIG. 2.

Referring to FIG. 3, the optical scanning system includes an angioscope catheter 24 which houses an angioscope 26 which is attached to the video camera and light source 14. As stated above, the output signal of the video camera, designated "28" in FIG. 3, is provided both to a live monitor A and to the digitization board 12 for digitization and viewing on monitor B in real time, as will be described in greater detail below. The light source, designated "30" in FIG. 3, attaches to the eyepiece 26a of the angioscope 26.

Referring to FIGS. 4A-4D, according to a preferred embodiment of the present invention, the angioscope catheter 24 comprises an inner catheter 32 which slides longitudinally with respect to an outer sheath 34. The outer sheath 34 includes a plurality of slitted sections 36 formed circumferentially near its distal end. The outer sheath 34 is bonded to the inner catheter 32 at their distal-most points. Thus, when the inner catheter 32 is pulled proximally with the outer sheath 34 held fixed, the slitted sections 36 of the outer sheath 34 splay out radially from the axis of the catheter 32 in a symmetrical fashion. This centers the angioscope during visualization, particularly in curved sections of the vessel, as best shown in FIGS. 4C and 4D. At the same time, it allows blood to flow in the vessel during the angioscopy procedure.

The angioscope 26 comprises an illuminated fiberoptic scope which extends through the inner catheter 32 for viewing through the open distal end of the catheter 32. The fiberoptic scope 26 may be of the lighted type manufactured by Baxter, Edwards LIS Division, Santa Ana, Calif. Such scopes have central viewing strands which are surrounded by peripheral illuminating strands. Although not illustrated in FIGS. 4A-4D, it should be understood that the proximal end of the scope 26 would be secured to the video camera and light source 14, as shown in FIG. 3.

As further shown in FIG. 4A, the angioscope centering catheter 24 also includes an irrigation port 38 for pulsatile irrigation of the vessel through the inner catheter 32. The angioscope 26 is held in place within the inner catheter 32 by means of an O-ring seal 40. A second O-ring seal 42 prevents blood from seeping out between the inner catheter 32 and the outer sheath 34. This second O-ring seal 42 slides longitudinally along a rigid section 44 that houses the inner catheter 32 to provide the splaying of the slitted sections 36 as described above. The rigid section 44 permits easy movement of the outer sheath and the inner catheter with respect to one another.

The angioscope centering catheter 24 described above is the subject of co-pending U.S. Patent Application Ser. No.707/187482, now U.S. Pat. No. 4,878,893, filed by Dr. Albert K. Chin of even date herewith, which application is commonly-assigned herewith to Dr. Thomas J. Fogarty and is hereby incorporated by reference as providing additional background for the present invention.

Referring back to FIG. 3, the angioscope centering catheter 24 is irrigated with sterile saline via the irrigation port 38 by means of an irrigation line 46 connected to a pressure vessel 48. The pressure vessel 48 houses a bag 50 of sterile saline which is attached to the irrigation line 46 by means of an irrigation line spike 52. An O-ring 54 seals the irrigation line spike 52 against the cover of the pressure vessel 48. Compressed air is supplied to the pressure vessel 48 via an air pressure inlet 56. The pressure within the vessel 48 is adjusted by a regulator 58 and is measured by pressure gauge 60.

As stated above, pulses of pressurized saline are delivered to the irrigation port 38 on command from the computer system, which opens and closes a solenoid pinch valve 30. The solenoid pinch valve 30 pinches a section of silicone tubing 64 which lies in line with the irrigation line 46. The computer system may be programmed to deliver a sequence of timed irrigation pulses or a single pulse may be delivered by means of the foot pedal switch 34 connected to the central processing unit 10 via communications and relay board 32.

A saline flush pulse is activated for a duration of approximately one second, the duration of the pulse being dependent upon the patient, the size of the vessel and the type of catheter used. This is in contrast to the constant flush which is maintained during present angioscopic procedures. The clear analog image of the interior of the vessel which is captured by the camera during the flush is digitized and displayed on monitor B and the image is frozen until the next flush cycle.

A stable monitor image is desired, with no black screen or interrupted images between monitor picture changes. This requires storage of the incoming image from the angioscope 34. Therefore, the analog image signal generated by the video camera 28 is digitized, stored in memory of the computer system and projected on video monitor B. The image is refreshed continuously, preferably at a rate of at least 30 times per second, until the image is changed with the next flush cycle, as illustrated in FIGS. 5A-5H; the eye can perceive no black screen or interruption of the image at this speed of image refreshing.

Figures 6A, 6B:
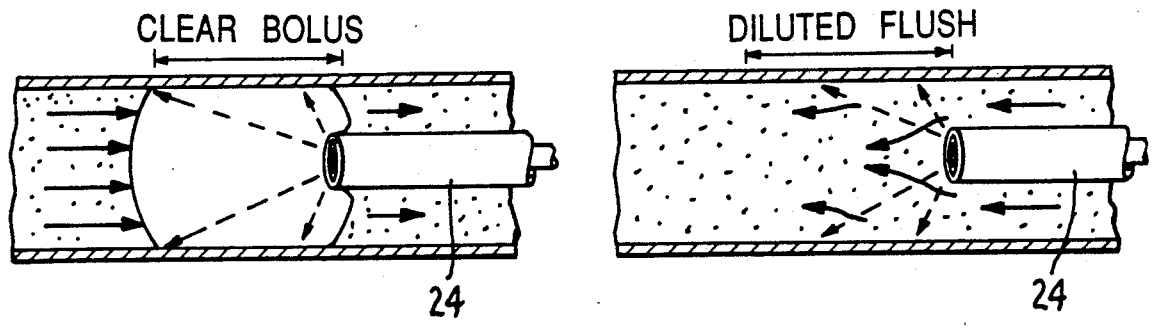
FIG. 6A is a cross-sectional view illustrating the use of a catheter for saline flush against blood flow.
FIG. 6B is a cross-sectional view illustrating the use of a catheter for saline flush with blood flow.

As stated above, it is difficult to obtain a bloodless viewing field in the arteries because of the higher pressure and flow rate of blood in these vessels. Therefore, as shown in FIG. 6, it is preferred that the angioscope 24 be inserted in the vessel such that the saline flush is directed against the direction of blood flow to create a bolus of saline flush solution that is visually clear for the focal distance of the angioscope 24. For the fiber optic scope identified above, this distance is approximately 15 mm. The flush is directed against the blood flow to achieve clearing with the minimal amount of saline. Experiments have shown that the flush stream is diluted if flushing is in the direction of blood flow, as shown in FIG. 6A, and clearing is only obtained with large volumes of flush. On the other hand, flushing against the blood flow establishes a clear area where opposing fronts of flush and blood flow meet.

Figure 7:
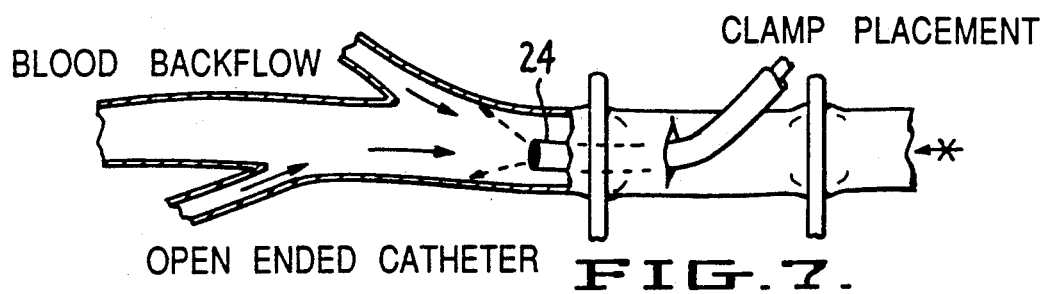
FIG. 7 is a cross-sectional view illustrating intraoperative angioscopy.

The catheter design used to flush against blood flow will vary with the situation and application. For intraoperative angioscopy, the artery will be isolated in the operating room, and an arteriotomy made to admit the angioscope. As shown in FIG. 7, the artery will be clamped proximal and distal to the arteriotomy site. If the angioscope 24 is advanced in a distal direction, there is no forward blood flow, only backflow from collateral side branches. Thus, the flushing catheter may be a straight, open ended catheter. If the angioscope is advanced in a proximal direction, it is again going against blood flow and a straight, open ended catheter will again be appropriate.

For percutaneous angioscopy, the angioscope is introduced via a needle puncture and an introducing sheath into the artery. Usually, the access site is the femoral artery. If the angioscope is threaded distally, it lies in the same direction as the blood flow. The catheter must now flush backwards to form a bolus which goes against the blood flow. As shown in FIGS. 8A and 8B, such a catheter may include a port which allows the flushing fluid to hit a deflecting shield at the distal tip of the angioscope, thus causing the flush to stream backwards. (A catheter that implements this type of deflector is disclosed in the above-referenced patent application by Dr. Chin.) If the angioscope is threaded proximally, a straight, open ended catheter will be used.

The timing of the flush is important. In the peripheral arteries, the blood flow may come to a standstill or even reverse its direction of flow in diastole. On the other hand, in the coronary arteries, forward blood flow occurs during diastole. The flush may be timed with the cardiac cycle of systole and diastole by triggering the flush with an electrocardiogram. An electrode pickup may be input to the computer to control the flush cycle.

Figure 5:
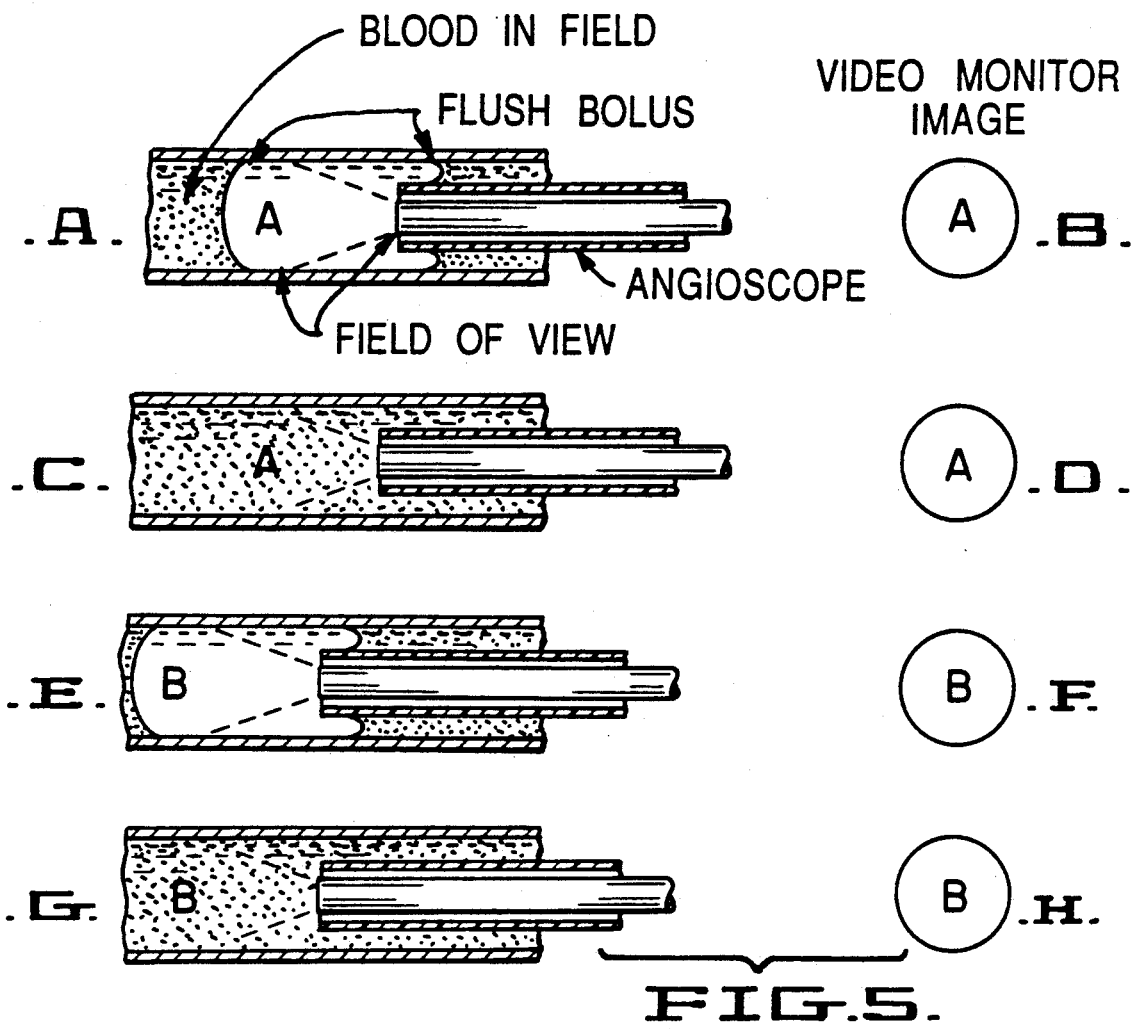
FIGS. 5A-5H provide a series of schematic drawings illustrating a synchronized flush/imaging sequence in accordance with the present invention.
FIG. 5I is a timing diagram illustrating an automatic synchronized flush/imaging sequence in accordance with the present invention.
Figure 5I:
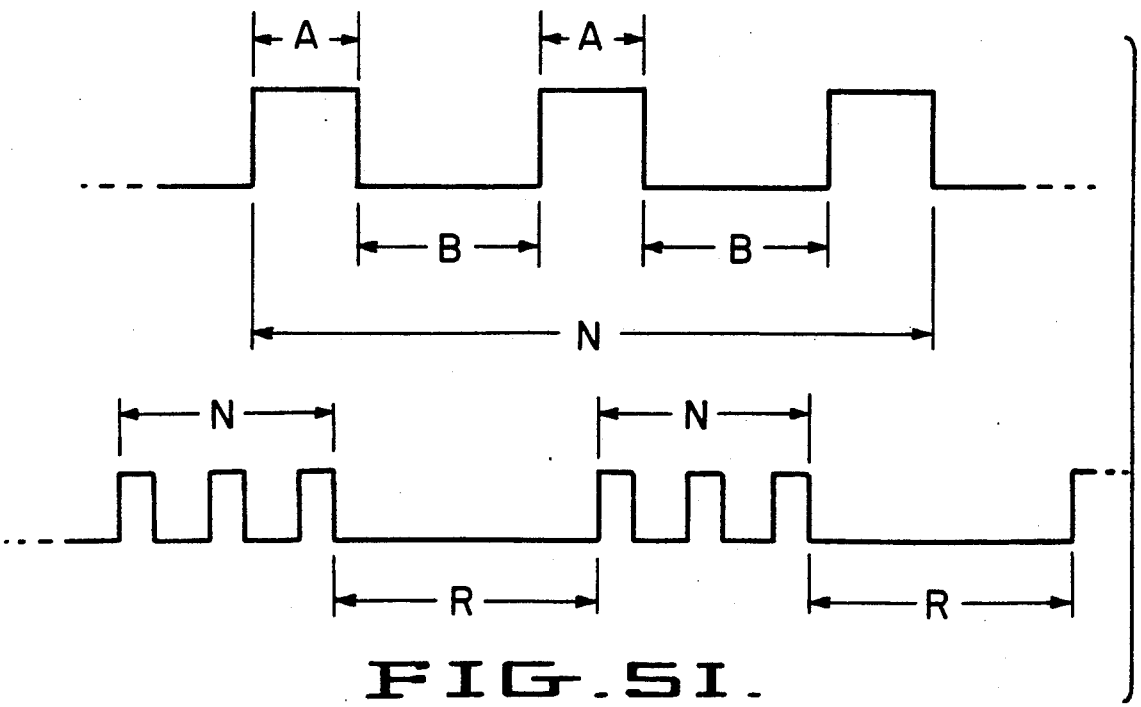

Capture of the monitor image may be performed in several different ways. The image capture following the flush may simply occur at a fixed time interval, as shown in the flush cycle sequence provided in FIG. 5I. FIG. 5I shows a flush cycle N that includes three flush pulses per cycle. Each flush pulse is of duration A, followed by a flush-interrupted period B. R designates the "rest" time between cycles. An updated image is "frozen" on each falling edge of the "A" flush pulse. Alternatively, the image capture may be triggered by the computer controls. For example, a densitometer may be used to detect the presence of a clear optical field. The clear field may also be determined by examining the maximal image contrast obtained during the flush cycle, and capturing the image when the image contrast just starts to decrease from its optimal degree.

Alternatively, as stated above, control of the flush cycle may be performed by the operator via the foot pedal switch which activates both the flush and image capture functions. A single depression of the pedal followed by its release may correspond to a single flush. Continued depression of the foot pedal may then result in a repeated flush cycle at specified time intervals; for example, at one second intervals. This allows angioscope advancement at a rate of 1.5 cm per second, with visualization of the entire length of the artery, while allowing normal blood flow to occur during the flush interrupted cycles.

Referring back to FIG. 1, both the color video display monitor A used for displaying the continuous live image produced by the camera and the analog RGB monitor B used for displaying the digital image produced by the imaging system are, for best results, high resolution monitors such as a Sony CPD-1303 or Taxan 770 monitor. The system status monitor C may be an industry standard monochrome monitor such as a Samsung amber monitor.

An AT compatible monographics serial interface I/O card 22 of generic manufacture is used to drive the monochrome monitor C and provide standard RS-232C communications.

A specialized digitization board 12, illustrated in FIG. 9, converts NTSC video images to a digitally generated facsimile represented on RGB monitor B. The board is the TARGA 16 product of Truevision Corp., Indianapolis, Indiana, which has been modified as illustrated in FIG. 9 for compatibility with the angioscopy imaging system of the present invention.

The changes made to the Truevision board were primarily for the purpose of improving speed and resolution. Capacitance and crystal adjustments were made to provide higher speed. Resistive adjustments were made to improve resolution. New jumper configurations were provided to improve the compatability of the video synch signals. The generic LM386 and 74138 components used by Truevision were replaced with more reliable National Semiconductor components.

A high resolution CCD camera and high intensity quartz light are used to provide a high resolution image to the system. The CCD camera is connected to the fiber optic angioscope, as described above. The light source is connected to the illuminating stands of the scope. In the preferred embodiment, the CCD camera is a Sony CCD color chip camera, Model No. DXC102, and the light is a generic 12Vdc 150W quartz bulb.

The communications and relay board, designed and manufactured by Nobles/Lai Engineering Inc., Carson, Calif., allows the central processing unit 10 to communicate with the solenoid.

Figure 10:
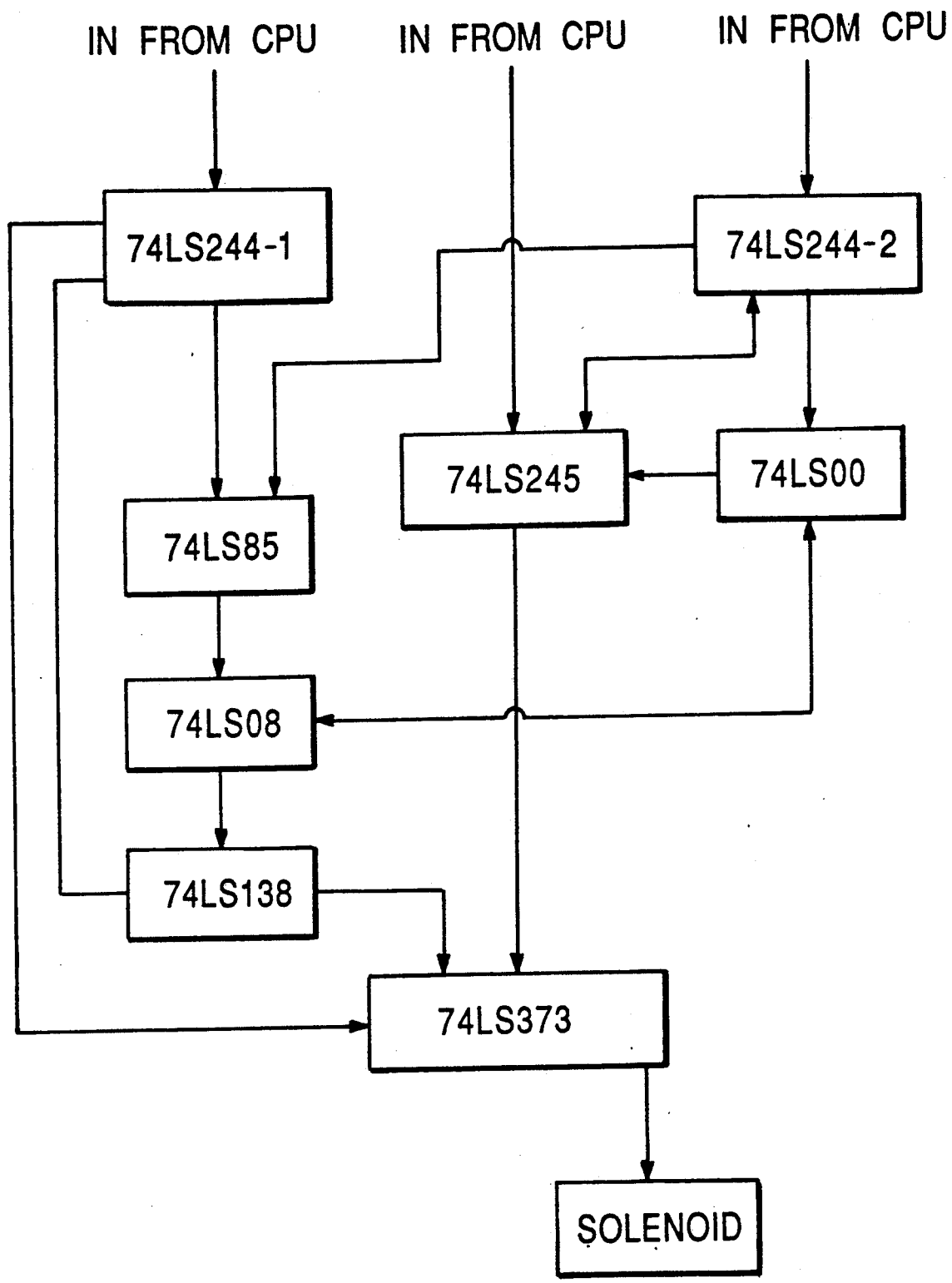
FIG. 10 is a schematic diagram illustrating a communications relay board utilized in the angioscopy imaging system shown in FIG. 1.

The communications and relay board is illustrated schematically in FIG. 10.

The 74LS244-1 component is a byte wide line driver the enable pins of which are tied to ground. Since the enable signal is active low, this chip always passes the address lines from the central processing unit 10 to the communications relay board. The 74LS244-2 component is an identical byte wide line driver whose enable pins of which are also tied to ground. Since the enable signal for this driver is active low, it, too, always passes the address and I/O lines from the central processing unit to the communications relay board. The 74LS245 component is a bi-directional buffer used to buffer the data bus in from and out to the central processing unit 10 to the communications relay board. The 74LS00 and the 74LS08 components are simple gates used to configure inputs to the 74LS138 and 74LS245. The 74LS85 component is used as a comparator to supply a toggle on its output pin when the inputs from the two 74LS244 components are equal. The 74LS138 is a 3-to-8 bit decoder used to further decode the address bus to deliver 32 consecutive addresses to the 74LS373 component.

The 74LS373 is an 8 bit shift register used to supply a signal to the solenoid.

The foot pedal is a simple, generic N/O (Normally Open) momentary SPST (Single Pull Single Throw) switch which provides simple control of irrigation and image capture.

The solenoid is an activated pinch valve which is controlled by the central processing unit 10 via the communications and relay board to regulate the flow of sterile saline to the catheter for irrigation of the vessel, as described above.

The central processing unit 10 is an AT PC motherboard based on an Intel 80286 CPU. It is a 12MHz based system with 1 Mbyte on-board RAM.

The handset allows the surgeon or technician fast and easy access to the different modes and functions of the system. The handset is designed with a roller ball for quick changes.

Figure 11:
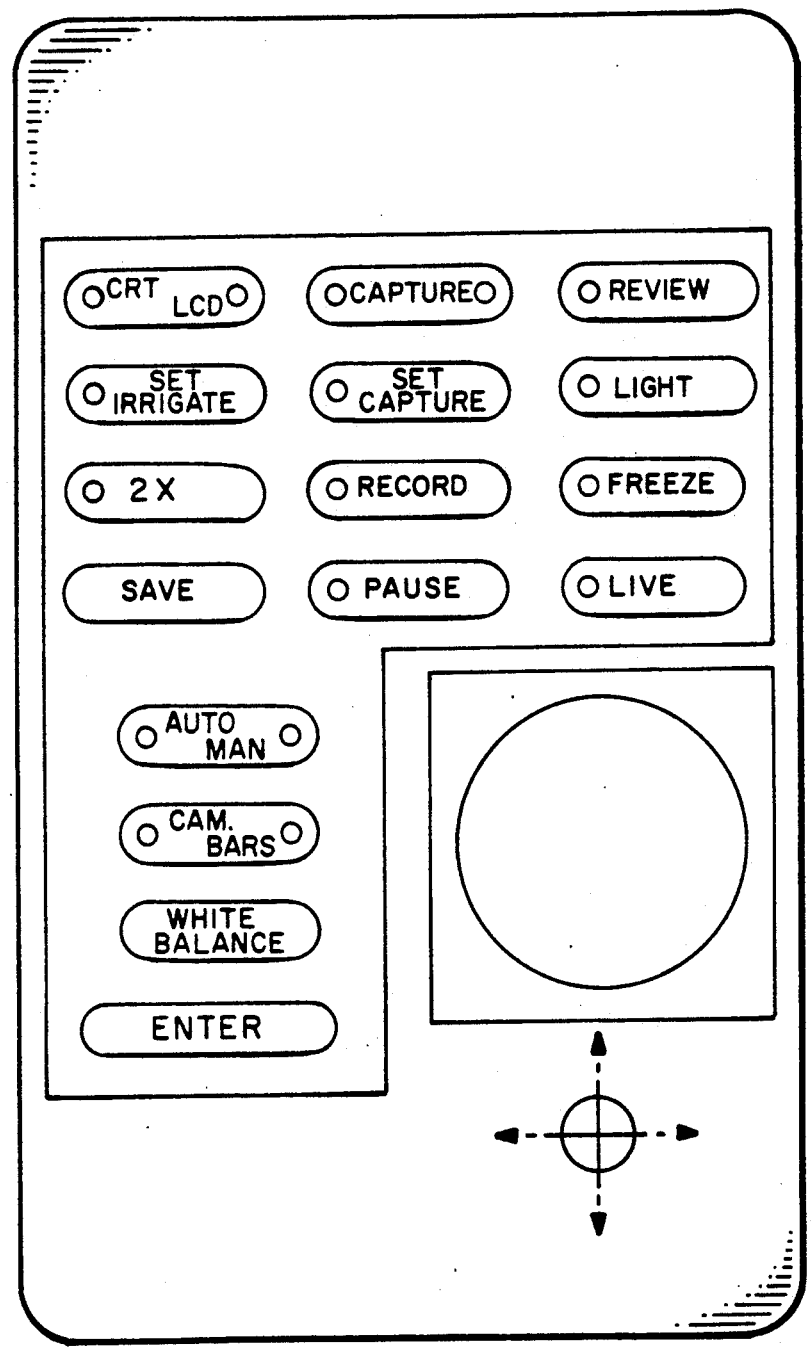
FIG. 11 is a pictorial illustration of a handset utilized in the angioscopy imaging system shown in FIG. 1.
Figure 12:
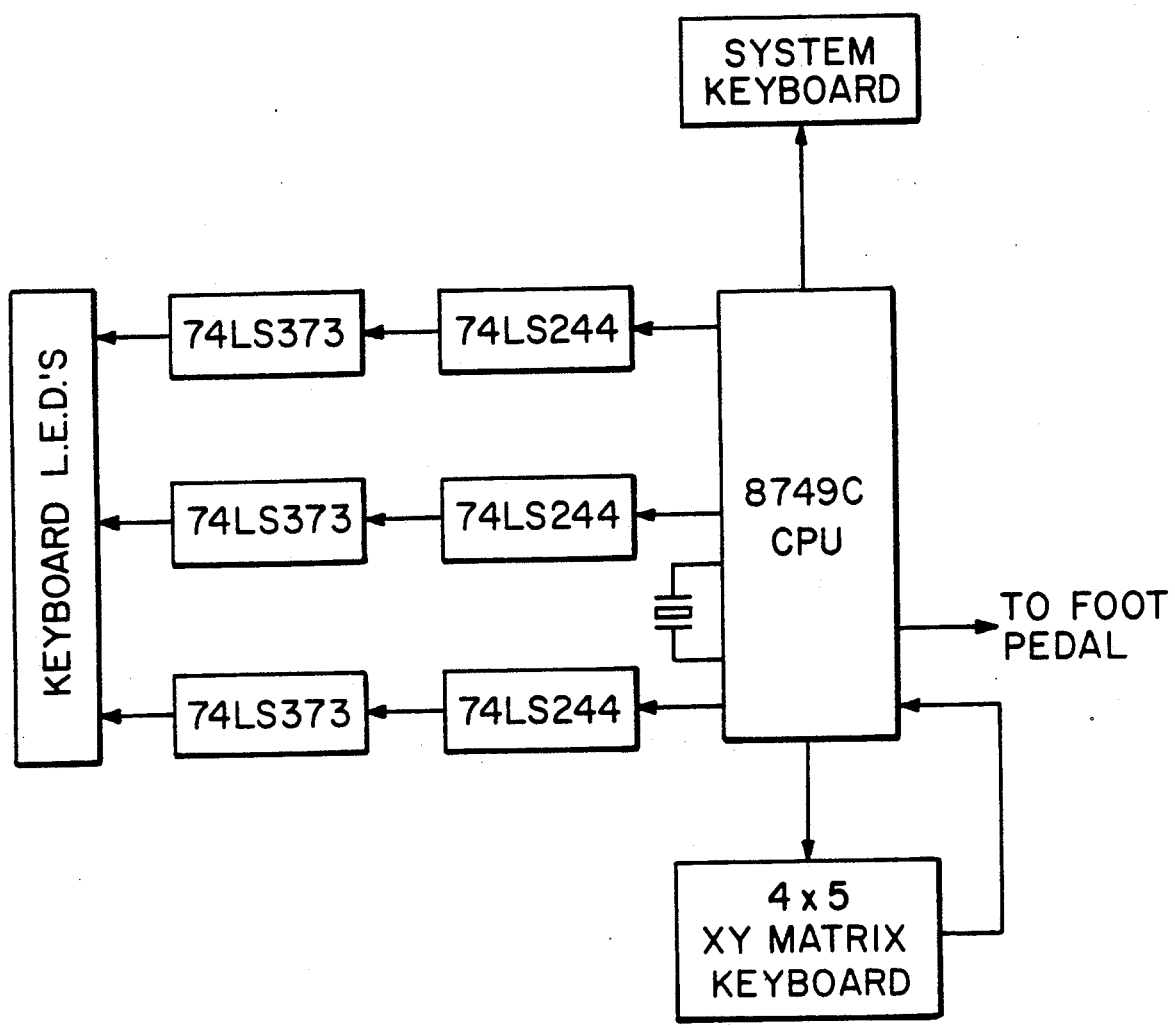
FIG. 12 is a schematic diagram illustrating the circuitry of the handset shown in FIG. 11.
Figure 13:
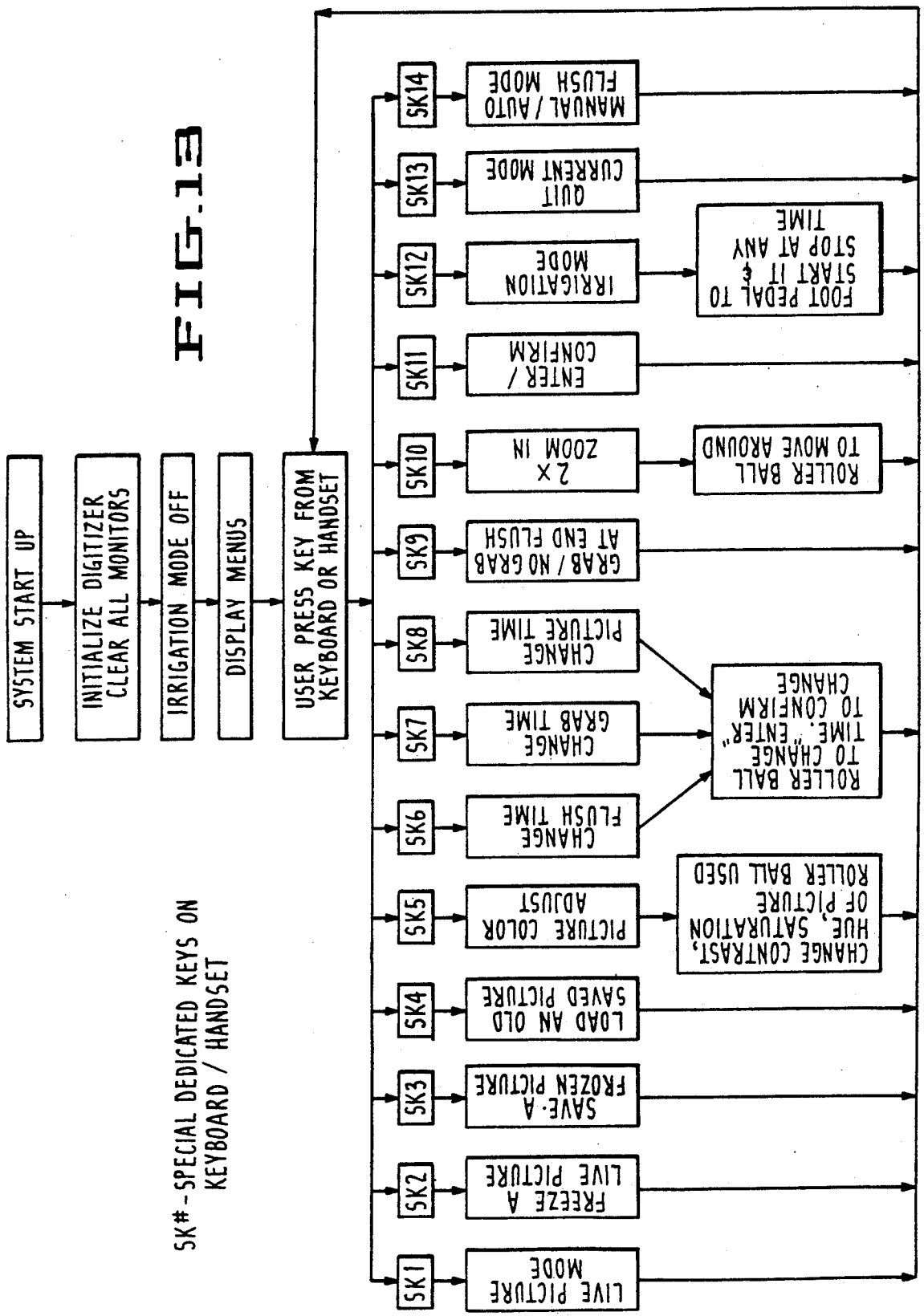
FIG. 13 is a flow sheet illustrating the function of the software provided in Appendix A.

The handset is shown pictorially in FIG. 11 and its circuitry is shown schematically in FIG. 12.

The three 74LS244 chips are used to buffer the inputs to the 74LS373 chips. The 74LS373 chips are used as 8 bit shift registers and are used to drive the handset LEDs. The 11 Mhz crystal provides the clock and timing for the 8749 CPU. The $4 \times 5$ XY matrix keyboard is a 20 key keyboard including 16 momentary push keys and 4 momentary toggle keys for the roller ball. The 8749C is a stand-alone microprocessor designed for keyboard encoding. In this application, it allows the handset keys to emulate function keys of the system keyboard. The foot pedal is a function of the keyboard, emulates a single-function key and is fed into the $4 \times 5$ matrix of the 8749C component.

The keyboard is a standard AT-style keyboard (e.g., Harvest 86-KEY) which allows the user to manually enter the same data as entered from the handset as well as alpha-numeric data (e.g., patient information).

A disk controller is required to provide communications between the 80286 motherboard and both the hard disk drive and the floppy disk drive. The controller used in this application is generic in manufacture and can be any AT compatible controller capable of handling at least a 1.2 MByte floppy disk drive and a 30 Mbyte hard disk drive.

The system software and all its necessary functions are all located on a user system disk, placed internally in the system. The system disk will start up the entire system when power is applied to the computer, checking each component for failures, and reporting any malfunctions onto the user screen. Using the user-friendly technique, all menus and status are easy to read and understand.

The software is written in C86 C language. Most of its function calls are dedicated to the digitizer board for image capturing and image processing. A source listing of the program is provided at the end of this specification as Appendix A.

It should be understood that the invention is not intended to be limited by the specifics of the above-described embodiment, but rather is defined by the accompanying claims.

```
/*
 *   SURGICAL ANGIOSCOPY IMAGE DIGITIZER PROGRAM
 *
 *   Release  2.11
 *   Date :   4-18-88     ( Last update )
 *   Designer : ALex Kwok-Yeung, Lai      ( Software )
 *              Anthony Nobles             ( Hardware )
 *   Company  : NOBLES/LAI Engineering
 *
 *   Description :
 *
 *
 *
 *
 *
 *
 *
 *
 *              1st printer port to control solenoid,
 *              2nd printer port take foot pedal control.
 *
 *              Using Function keys & pad as inputs.
 *
 */
#include "stdio.h"          /* standard I/O file */
#include "tardev.h"
#define TIMER_LO 0x46C      /* tick counter for timer  */
#define PAGE 0               /* defining constants */
#define SPACE  0x20
int     tpnum, maxcycle , stoptime ;
float   tdur,tndur,tintrvl,tmandur,tolive,tgrab  ;

/*      tdur   - duration time which the device is on.
 *      tpnum  - number of durations in one cycle.
 *      tndur  - device down time before next duration on.
 *      tintrvl - the elapse time between cycles.
 *      tmandur - manual duration time.
 *      tolive  - time which live picture comes on in duration.
 *      tgrab   - time to grab an image.
 *      maxcycle - maxium cycles in one automatic period.
 */
int     cntrl_flag=1 ;           /* 1=auto, 0=manual */
int     grab_flag = 1 ;          /* 1=grab , 0=no grab */
char    beep='\007' ;

extern struct TARStruct *targa ;
extern struct M8Struct *m8 ;

APPENDIX A ain()

int   i,j ;
   char  ch,dh ;
   char  filename[20] ;      /* user input file name    */ extern int tpnum,maxcycle, stoptime  ;
   extern float tdur,tndur,tintrvl,tmandur,tolive,tgrab ;
   extern int bdos() ;       /* bios service routines   */ bdos(5,'B') ;     /* turn off bit 0 in parallel port */
   stoptime = 0 ;
   tpnum=maxcycle=1 ;
   tdur=tndur=tintrvl=tmandur=tolive=tgrab=0.5 ;
```

```
greeting() ;
GraphInit(-1) ;              /* init TARGA board */
system("cls") ;
menu() ;
status() ;                   /* status of the control device */
printf("\n") ;
SetLiveMode() ;              /* live mode      */
bdos(9," Press Red keys          $") ;
 do (
     ch = bdos(8) & 0xff ;
   ) while ( ch != 0x00 ) ;
ch = bdos(8) & 0xff ;       /* get red key codes        */
while ( ch != 'S')          /*    DEL key   */
 {
    switch (ch)
    {
      case 'K':     /*    <- key    */
             bdos(2,0x0D) ; bdos(2,0x0A) ;  /* CR-LF */
             bdos(9," Going to Live Picture Mode $");
             SetLiveMode() ;
             system("cls") ; menu() ;
             bdos(2,0x0A) ; bdos(2,0x0A) ;
             status() ; break;
      case 'G':     /*   HOME key    */
             bdos(2,0x0D) ; bdos(2,0x0A) ;  /* CR-LF */
             bdos(9," Save the Captured Picture. $") ;
             printf("\nEnter Save under filename : ") ;
             gets(filename) ;
             printf("\nFile is being saved. Please Wait ...\n") ;
             PutPic(filename,0,0,-1,-1,-1) ;
              system("cls") ; menu() ;
             bdos(2,0x0A) ; bdos(2,0x0A) ;
             status() ; break ;
      case 'M':      /*     ->      */
             bdos(2,0x0D) ; bdos(2,0x0A) ;  /* CR-LF */
             bdos(9," Freeze the Picture. $") ;
             GrabFrame() ;
             SetDispMode() ;
             system("cls") ; menu() ;
             bdos(2,0x0A) ; bdos(2,0x0A) ;
             status() ;break ;
      case 'I':      /*  PgUP   key    */
             bdos(2,0x0D) ; bdos(2,0x0A) ;  /* CR-LF */
              bdos(9," Retreive a Captured Picture. $") ;
              printf("\nEnter Picture file to be Retrieved : ");
              gets(filename) ;
              printf("\nPicture is now being Retrived.") ;
              printf(" Please Wait... \n") ;
              GetPic(filename,-1,-1,-1) ;
             SetDispMode() ;
             system("cls") ; menu() ;
             bdos(2,0x0A) ; bdos(2,0x0A) ;
             status() ; break ;
      case 'O':            END  key    */
             bdos(2,0x0D) ; bdos(2,0x0A) ;  /* CR-LF */
             bdos(9," Change Irrigation Control.$") ;
             if (cntrl_flag) cntrl_flag = 0 ;
             else            cntrl_flag = 1 ;
                system("cls") ;
                menu() ; bdos(2,0x0A) ; bdos(2,0x0A) ;
             status() ; break ;
```

```c
        case 'Q' :    /*    PgDN   key   */
                bdos(2,0x0D) ; bdos(2,0x0A) ;   /* CR-LF */
                 bdos(9," Start Irrigation Procedure. $") ;
                 if (cntrl_flag) automode() ;
                 else            manmode() ;
                    system("cls") ;
                  menu() ; bdos(2,0x0A) ; bdos(2,0x0A) ;
                 status() ; break ;
        case 'B' :    /*    F8  key   */
                 if (grab_flag) grab_flag = 0 ;
                 else           grab_flag = 1 ;
                 printf("\n Grabbing is now ");
                 if (grab_flag) printf(" Freezing at end.\n");
                 else           printf(" NO freezing at end.\n");
                 break ;
        case 'R':     /*    INS   key   */
                 picturejust() ;
        default :
                 printf("Wrong Key - Try again \n") ;
        }
    bdos(2,0x0D); bdos(2,0x0A) ;
    printf(" Press Red Key              ") ;
    do {
        ch = bdos(8) & 0xff ;
      } while ( ch != 0x00 ) ;
    ch = bdos(8) & 0xff ;
     if (ch == 'S') {
           printf("\nDo you really want to quit ? \n") ;
           printf(" Hit Y to quit, or any other key to continue. ");
           ch = bdos(1) & 0xff ;
           if ((ch == 'Y') || (ch == 'y')) break ;
         }
    }

GraphEnd() ;                /*  return icb memory  */
   system("cls");
   printf("\n\n Program done, and All ends Well !! \n") ;
}
/*********** greeting ***********/
greeting()
{
   char ch ;

system("cls") ;
   printf("\n\n                          ");
   printf("W e l c o m e   T o \n");
   printf("\n                    ");
   printf("T h e   F a s c i n a t i n g   W o r l d \n");
   printf("\n                    ");
   printf("O f   B i o m e d i c a l   T e c h n o l o g y \n");
   printf("\n\n                ");
   printf("A N G I O S C O P Y   I M A G E   D I G I T I Z E R \n");
   printf("                                                 ") ;
   printf(" Release 2.11 \n");
   printf("\n\n\n                                          ");
   printf(" Nobles/Lai Engineering \n");
   printf("                                ");
   printf("940 E. Dominguez Ste. K ,Carson CA. 90746 \n") ;
   printf("Copyright @1988. Mar  MCMLXXXVIII2-11 \n");
   printf("                              Dr. Thomas F  arty \n") ;
   printf("\n                     ");
   printf(" Press the SPACE BAR to continue. ");
    ch= bdos(7) & 0xff ;       /* no echo on input */
    while ( (int) ch != SPACE ) ch = bdos(7) & 0xff ;
```

```
}
/************  menu  ************/
menu()
{
    bdos(2,0x0A); bdos(2,0x0A); bdos(2,0x0A) ;
    bdos(9,"                    $");
    bdos(9," M E N U    S E L E C T I O N $");
    bdos(2,0x0D) ; bdos(2,0x0A) ;
    bdos(9,"                    $");
    bdos(9,"===================================$");
    printf("\n\n  RED keys are for main menu selection. \n") ;
    printf("\n  BLUE keys are for irrigation uses only. \n") ;
}
/***********  status  ********/
status()
{
   printf("\n") ;
   printf("       CURRENT CONTROL SETTINGS     ");
   printf("\n        =========================== \n\n");
   printf("  Irrigation Flush Time             : ");
   printf("%0.2f secs.\n",tdur) ;
   printf("  Live Picture Starting Time        : ");
   printf("%0.2f secs.\n",tolive ) ;
   printf("  Image Grab Time (from start)    : ") ;
   printf("%0.2f secs.\n",tgrab) ;
   printf("  Irrigation Pause Time           : ") ;
   printf("%0.2f secs. \n",tndur) ;
   printf("  Number of Flushings   / cycle : ");
   printf("%d \n",tpnum) ;
   printf("  At  Rest  Cycle  Time           : ");
   printf("%0.2f secs. \n",tintrvl);
   printf("  Maxium cycles in whole period : ");
   printf("%d \n",maxcycle) ;
   printf("  Current Flushing Control is       --> ");
   if(cntrl_flag) printf(" AUTOMATIC \n");
   else           printf(" MANUAL \n");
   printf("  Current Grabbing Control is       --> ");
   if( grab_flag) printf(" Freezing at end \n") ;
   else           printf(" No freezing pictures \n") ;
   printf("\n") ;
}
/***********  manual  status  ********/
man_status()
{
   printf("\n") ;
   printf("       CURRENT CONTROL SETTINGS     ");
   printf("\n        =========================== \n\n");
   printf("  Irrigation Flush Time             : ");
   printf("%0.2f secs.\n",tmandur) ;
   printf("  Live Picture Starting Time        : ");
   printf("%0.2f secs.\n",tolive ) ;
   printf("  Image Grab Time (from start)    : ") ;
   printf("%0.2f secs.\n",tgrab) ;
   printf("  Current Grabbing Control is       --> ");
   if( grab_flag) printf(" freeze at end  \n") ;
   else           printf(" No Freeze at end \n") ;
   printf("\n") ;
}
/*********  chg_ift  ************/
chg_ift()
{
   char ch ;   int kj ;
   printf("\n");
```

```c
        printf(" Irrigation Flush Time          : ");
        printf("%0.2f secs. \n",tdur);
        printf(" Enter new settings ? ") ;
        while ( key_scan() == -1 ) ;
        kj = key_scan() ;
        if (kj == 0x1C0D) return ;
        if ( isdigit(kj) )
           {
                scanf("%f",&tdur) ;
                getchar() ;
                if (tdur < 0.2) tdur = 0.2 ;
                tmandur = tdur ;
           }
 }

/********** chg_pgt *************/
hg_pgt()
 {
    char ch ; int kj ;
    printf("\n");
    printf(" Picture Grab Time       : ");
    printf("%0.2f secs. \n",tgrab) ;
    printf(" Enter new settings ? ") ;
    while ( key_scan() == -1 ) ;
    kj = key_scan() ;
    if (kj == 0x1C0D ) return ;
    if ( isdigit(kj) )
       {
            scanf("%f",&tgrab) ;
            getchar() ;
            if ((tgrab < 0) || (tgrab > tdur)) tgrab = tdur ;
       }
 }

/************* chg_lcot **********/
hg_lcot()
 {
    char ch ; int kj ;
    printf("\n Live Picture starting time      : ");
    printf("%0.2f secs. \n",tolive);
    printf(" Enter new time ? ") ;
    while (key_scan() == -1) ;
    kj = key_scan() ;
    if( kj == 0x1C0D ) return ;
    if (isdigit(kj))
       {
            scanf("%f",&tolive) ;
            getchar() ;
            if ((tolive < 0 ) || (tolive > tdur))  tolive = 0 ;
       }
 }

/************ chg_ipt *************/
hg_ipt()
 {
    char ch ; int kj ;
    printf("\n Irrigation Pause Time      : ");
    printf("%0.2f secs. \n",tndur);
    printf(" Enter new time ? ") ;
    while ( key_scan() == -1 ) ;
    kj = key_scan() ;
    if (kj == 0x1C0D ) return ;
    if ( isdigit(kj) )
       {
```

```c
        scanf("%f",&tndur) ;
        getchar() ;
        if ( tndur < 0.1 ) tndur = 0.1 ;
    }

/*************** chg_nfc ************/
g_nfc()
{
  char  ch ;  int  kj ;
    printf("\n Number of Flushings per Cycle : ");
    printf("%d \n",tpnum) ;
    printf(" Enter new number ? ") ;
    while ( key_scan() == -1 ) ;
    kj = key_scan() ;
    if ( kj == 0x1C0D ) return ;
    if ( isdigit(kj) )
       {
          scanf("%d",&tpnum) ;
          getchar() ;
          if ( tpnum < 1 )   tpnum = 1 ;
       }
}

/*********** chg_rct ********/
hg_rct()
{
  char  ch ;   int kj ;
    printf("\n At  Rest  Cycle  Time         : ") ;
    printf("%0.2f secs. \n",tintrvl);
    printf(" Enter new rest time ? ") ;
    while ( key_scan() == -1 ) ;
    kj = key_scan() ;
    if ( kj == 0x1C0D ) return ;
    if ( isdigit(kj) )
       {
          scanf("%f",&tintrvl) ;
          getchar() ;
          if ( tintrvl < 0.1 )  tintrvl = 0.1 ;
       }
}

/*********** chg_ncp **********/
hg_ncp()
{
   char  ch ;   int  kj ;
    printf("\n Maxium number of cycles / period : ");
    printf("%d \n",maxcycle) ;
    printf(" Enter new period cycle number ? " ) ;
    while ( key_scan() == -1 ) ;
    kj = key_scan() ;
    if (kj == 0x1C0D ) return ;
    if ( isdigit(kj) )
       {
          scanf("%d",&maxcycle) ;
          getchar() ;
          if ( maxcycle < 1 )  maxcycle = 1 ;
       }
}
/******  manmode() ******/
manmode()
{
  int  lptst, ntmandur, ntlive , ntgrab ;
  char  ch ;   int   j ;
```

```
   man_start :
     system("cls") ;
     man_status() ;
     printf("\n BLUE key selections... \n") ;
     for (;;) {
        do { ch = bdos(8) & 0xff ; } while (ch != 0x00 ) ;
        ch = bdos(8) & 0xff ;
        switch (ch)

{
      case ';' :       /* F1 key   */
               chg_.t() ;
               break ;
      case '<' :       /* F2 key   */
               chg_pgt() ;
               break ;
      case '=' :       /*   F3 key   */
               chg_lcot() ;
               break ;
      case 'B' :       /*   F8 key  */
               if (grab_flag) grab_flag = 0 ;
               else             grab_flag = 1 ;
               printf("\n Grabbing is now ");
               if (grab_flag) printf(" Freezing at end.\n");
               else           printf(" NO freezing at end.\n");
               break ;
      case 'S' :       /*  DEL key  */
      case 'C' :       /*   F9 key  */
      case 'D' :       /*  F10  key */
               break ;
      default  :  printf(" Wrong key - try again . \n") ;
   }
   if (ch == 'S') break ;
   if (ch == 'C') break ;
   if (ch == 'D') break ;
system("cls") ;
printf("\n MANUAL IRRIGATION CONTROL MODE \n\n") ;
 man_status() ;
 }
 if (ch == 'S') goto man_out ;
 if (ch == 'D') goto man_out ;
 if ((tolive >= tmandur) || (tolive < 0))  tolive = 0 ;
 if ((tgrab >= tmandur) || (tgrab < tolive)) tgrab = tmandur ;
 ntlive = (tolive * 1000) / 55 ;      /* live pic on time */
 ntmandur = (tmandur * 1000) / 55 ;   /* 55 msec loop count */
 ntgrab = (tgrab * 1000) / 55 ;       /*  grab time    */
 lptst = 0 ;
 system("cls") ;
 man_status() ;
 for (;;)                /* will exit only if q hit */
{
 stoptime = 0 ;
 lptst = 0 ;
 j = 0 ; ch = 'a' ;
    printf("\nPress  ANY KEY or FOOT PEDAL to start, or ") ;
    printf(" hit q  to quit at any time.") ;
    while (j == 0)
    {
        if (prt_err(1)) j = 1 ;
        else if (key_scan() != -1)
            {
              j = 1 ;
              ch = bdos(8) & 0xff ;
            }
```

```
            }
        if ( (ch == 'q') || (ch == 'Q')) break ;
        lptst = on_dur_man(ntmandur,ntlive,ntgrab) ;
        printf(" %d", stoptime * 55 ) ;
          for ( j = 1 ; j < 5000 ; j += 1 ) lptst += 1 ;   /* delay */
        }
    goto man_start ;
  man_out :
      printf("\n Quitting Maanual Procedure ....\n") ;
}

/****    automode()    ********/
                                            -24-
automode()
{
  int  kloop, nton, ntoff, ntrest, ntlive, lptst ,ntgrab ;
  char ch ;   int  j, jcycle ;

auto_start :
  system("cls") ;
  status() ;
    printf(" BLUE key selections ... \n") ;
    for (;;) {
        do { ch = bdos(8) & 0xff ; } while ( ch != 0x00 ) ;
        ch = bdos(8) & 0xff ;
        switch (ch)
        {
          case ';' :     /*   F1   key    */
                 chg_ift() ;
                 break ;
          case '<' :     /*   F2   key    */
                 chg_pgt() ;
                 break ;
          case '=' :     /*   F3   key    */
                 chg_lcot() ;
                 break ;
          case '>' :     /*   F4   key    */
                 chg_ipt() ;
                 break ;
          case '?' :     /*   F5   key    */
                 chg_nfc() ;
                 break ;
          case '@' :     /*   F6   key    */
                 chg_rct() ;
                 break ;
          case 'A' :     /*   F7   key    */
                 chg_ncp() ;
                 break ;
          case 'B' :     /*   F8   key    */
                 if (grab_flag)  grab_flag = 0 ;
                 else            grab_flag = 1 ;
                 printf("\nGrabbing is now ") ;
                 if (grab_flag) printf("freezing.\n") ;
                 else           printf("NO freezing.\n") ;
                 break ;
          case 'C' :     /*   F9   key    */
          case 'S' :     /*   DEL  key    */
          case 'D' :     /*   F10  key    */
                 break ;
          default  : printf("Wrong Color Key - try again \n") ;
        }
        if (ch == 'S') break ;
        if (ch == 'C') break ;
        if (ch == 'D') break ;
```

```c
         system("cls") ;
         status() ;
           printf(" BLUE key selections ... \n") ;
           }
           if (ch == 'S')  goto auto_out ;
           if ( ch == 'D')  goto auto_out ;
          if ( tgrab < tolive)  tgrab = tdur ;
          if ( tolive >= tdur )  tolive = 0 ;
      nton = (tdur * 1000) / 55 ;        /* duration on period */
      ntoff = (tndur * 1000) / 55 ;      /* duration off period */
      ntrest = (tintrvl * 1000) / 55 ;   /* cycle rest time    */
      ntlive = (tolive * 1000) / 55 ;    /* live pic on time */
       ntgrab = ( tgrab * 1000 ) / 55 ;
      lptst = 0 ;
           for (;;)             /* only quit when hit q */
               {
               printf("\nPress A  KEY or FOOT PEDAL to star    or ") ;
               printf(" hit  q  to quit at any time.    ") ;
               j = 0 ;
               while ( j == 0)
                   {
                   if (prt_err(1))   j = 1 ;
                     else if (key_scan() != -1)
                         {
                         j = 1 ;
                         ch = bdos(8) & 0xff ;
                         }
                   }
               if ( (ch == 'q') || (ch == 'Q')) break ;
               jcycle = maxcycle ;
               while ( jcycle > 0 )
                   {
                   kloop = tpnum - 1 ;
                   lptst = on_dur_man(nton,ntlive,ntgrab) ;
                   if (lptst == 999) break ;
                   while (kloop > 0)
                       {
                       lptst = off_dur(ntoff);
                       if (lptst == 999) break ;
                       lptst = on_dur(nton,ntlive,ntgrab) ;
                       if (lptst == 999) break ;
                       kloop -= 1 ;
                       }
                   if (lptst == 999) break ;
                   lptst = off_dur(ntrest) ;
                   if (lptst == 999) break ;
                   bdos(6,7) ; bdos(6,7) ; bdos(6,7) ;
                   jcycle -= 1 ;
                   }
               for ( j = 1 ; j < 8500 ; j += 1 )  lptst += 1 ;
              }
         goto auto_start ;
         auto_out :
            printf("\n Quitting automatic procedure ... \n") ;
      }
      /******    duration_on    *****/
      on_dur(tsecs,lvtsecs,grabsec)
      int  tsecs , lvtsecs, grabsec  ;
      {
         unsigned  tickref,kbstat ;
         int  i, j, k ;
         unsigned int kbch ;
          char kch ;
```

```
bdos(5,'A') ;           /* turn bit 0 on in port */
i = 0 ;
while (tsecs >0)
 {
  if ( i >= lvtsecs ) SetLiveMOde() ;
  tickref = peek(TIMER_LO,0) ;
  while (tickref == peek(TIMER_LO,0)) ; /* equal after 55msec */
   if ( key_scan() != -1 )
       {
          kch = bdos(8) ;       /* non echo get char */
       if (grab_flag) {    GrabFrame() ;
                           SetDispMode() ;
                      }
          bdos(5,'B') ;       /* bit 0 off */
          return (999) ;      /* out and quit    */
       }
    else if ( prt_err(1) )
       {
          if (grab_flag) {    GrabFrame() ;       26-
                              SetDispMode() ;
          bdos(5,'B') ;       /* bit 0 off */
          return (999) ;      /* out and quit    */
       }
    tsecs -= 1 ;
    i += 1 ;
    j = i % 18 ;        /* 1 sec interval */
    if (j == 0) bdos(6,7) ;   /* second testing */
     if ( i >= grabsec )
       {
          if (grab_flag) {    GrabFrame() ;
                              SetDispMode() ;   }
          bdos(5,'B') ;
          return (0) ;
       }
 }
    bdos(5,'B') ;
        if (grab_flag) {    GrabFrame() ;
                            SetDispMode() ;   }
    return (0) ;        /* 0 => o.k. */

/****** duration_off *******/
ff_dur(tsecs)
nt tsecs ;

int i, j ;
  unsigned tickref ;
  char kch ;

bdos(5,'B') ;      /* bit 0 off */
  i = 0 ;
  while ( tsecs > 0)
  {
    tickref = peek(TIMER_LO,0) ;
    while (tickref == peek(TIMER_LO,0)) ;
     if ( key_scan() != -1 )
        {
                kch = bdos(8) ;
                return (999) ;
        }
     else if ( prt_err(1) )
        {
              return (999) ;
        }
```

```c
        tsecs -= 1 ;
        i += 1 ;
        j = i % 18 ;
        if (j == 0) bdos(6,7) ;        /* second testing  */
     }
     return (0) ;                      /* all o.k.  */

/**********    Picture  Adjusts  *********/
picturejust()
{
  int   kk ;
  char  dh ;

system("cls") ;
     printf("\n\n This procedure adjusts the following parameters : \n") ;
     printf("    - the Hue \n") ;
     printf("    - the Contrast \n") ;
     printf("    - the Saturation .....   of a  LIVE  PICTURE \n\n") ;
     printf(" Press ( H,C,S or Q to quit ) : ") ;
     dh = bdos(7) & 0xff ;
     while ((dh != 'Q') && (dh != 'q'))
     {
        switch (dh)
        {
          case 'H':
          case 'h':
                printf("Hue ,   Enter Level (0-31) : ") ;
                scanf("%d \n",&kk) ;  getchar() ;
                SetHue(kk) ;
                break ;
          case 'C':
          case 'c':
                printf("Contrast ,   Enter Level (0-31) : ") ;
                scanf("%d \n",&kk) ;  getchar() ;
                SetContrast(kk) ;
                break ;
          case 'S':
          case 's':
                printf("Saturation ,   Enter Level (0-7) : ") ;
                scanf("%d \n",&kk) ;  getchar() ;
                SetSaturation(kk) ;
                break ;
          default :
                printf("Unknown Command ??? \n") ;
        }
        printf("\n Press ( H,C,S or Q to quit ) : ") ;
        dh = bdos(7) & 0xff ;
     }
     printf(" Quit. \n") ;

/******   manual_duration_on   *****/
/*   difference with on_dur is that during the 1st three-
 *   quarter second of the starting of flushing, the
 *   program will not recognise the keyboard nor the
 *   foot-pedal, so that it will not detect a stop
 *   flushing false signal.
 */
on_dur_man(tsecs,lvtsecs,grabsec)
int  tsecs , lvtsecs , grabsec ;
{
    unsigned  tickref,kbstat ;
    int  i, j, k ;
    unsigned int kbch ;
    char kch ;
```

```
bdos(5,'A') ;              /* turn bit 0 on in port    */
i = 0 ;
while (tsecs >0)
 {
   if ( i >= lvtsecs ) SetLiveMOde() ;
   tickref = peek(TIMER_LO,0) ;
   while (tickref == peek(TIMER_LO,0)) ; /* equal after 55msec */
     if ( i >= 14 )
       {
         if ( key_scan() != -1 )
         {
           kch = bdos(8) ;        /* non echo get char */
           if (grab_flag) {       GrabFrame() ;
                                  SetDispMode() ;      }
           bdos(5,'B') ;          /* bit 0 off */
           return (999) ;         /* out and quit         */
          }
         else if ( prt_err(1) )
         {
           if (grab_flag) {       GrabFrame() ;
                                  SetDispMode() ;      }
           bdos(5,'B') ;          /* bit 0 off  */
           return (999) ;         /* out and quit         */
         }
        }
    tsecs -= 1 ;
    i += 1 ;
    steptime += 1 ;
    j =   i  % 18 ;       /* 1 sec interval */
    if (j == 0) bdos(6,7) ;   /* second testing  */
    if ( i >= grabsec )
       {
         if (grab_flag)    {  GrabFrame() ;
                              SetDispMode() ;     }
         bdos(5,'B') ;
         return (0) ;
       }
  }
bdos(5,'B') ;
       if (grab_flag) {    GrabFrame() ;
                           SetDispMode() ;
                      }
return (0) ;         /* 0 => o.k. */
```

What is claimed is:

1. An angioscopy imaging system for visualizing the interior of a vessel, such as an artery, the system comprising:

(a) a central processing unit;

(b) optical scanning means for insertion into the interior of the vessel for generating an image of the interior of the vessel, the optical scanning means being connected to the central processing unit for control thereby; and (c) irrigation means for introducing pulses of flush solution into the interior of the vessel to provide a clear viewing field within the vessel for the optical scanning means, the irrigation means being connected to the central processing unit for control thereby such that the generation of the image is synchronized with the pulsed introduction of flush solution.

2. An angioscopy imaging system as in claim 1 and further including input means connected to the central processing unit for introducing control commands to the central processing unit for controlling the optical scanning means and the irrigation means.

3. An angioscopy imaging system as in claim 2 and further including a system status monitor connected to the central processing unit for providing a listing of possible control commands to the central processing unit.

4. An angioscopy imaging system as in claim 3 wherein the system status monitor includes means for providing information relating to the status of the optical scanning means and the irrigation means.

5. An angioscopy imaging system as in claim 1 and further including a display monitor connected to the central processing unit for displaying the image generated by the optical scanning means.

6. An angioscopy imaging system as in claim 1 wherein the optical scanning means comprises means for digitizing the image.

7. An angioscopy imaging system as claim 6 and further including means for displaying the digitized image.

8. An angioscopy imaging system as in claim 6 and further including means for storing the digitized image.

9. An angioscopy imaging system for visualizing the interior of a vessel, such as an artery, the system comprising:
   (a) a central processing unit;
   (b) optical scanning means for insertion into the interior of the vessel for capturing a live image of the interior of the vessel;
   (c) a camera for receiving the live image captured by the optical scanning means and generating an electrical output signal representing the live image;
   (d) digitizer means for converting the electrical output signal to corresponding digital data, the digitizer means being connected to the central processing unit for receiving digitization control signals therefrom;
   (e) irrigation means for introducing flush solution into the interior of the vessel to provide a viewing field for the optical scanning means, the irrigation means being connected to the central processing unit for receiving irrigation control signals therefrom such that the conversion to digital data is synchronized with the introduction of flush solution; and
   (f) a monitor responsive to the digital data for displaying a digitized image representing the live image.

10. An angioscopy imaging system as in claim 9 and further including means for storing the digital data.

11. An angioscopy imaging system as in claim 10 wherein the irrigation means is responsive to irrigation control signals from the central processing unit to introduce a pulsatile sequence of flush solution to the interior of the vessel.

12. An angioscopy imaging system as in claim 11 wherein the digitizer means is responsive to digitization control signals to update the digital data provided to the monitor in synchronization with the pulsatile introduction of flush solution.

13. An angioscopy imaging system as in claim 12 wherein the digital data is provided to the monitor periodically between digital data updates to refresh the digital image displayed by the monitor.

14. An angioscopy imaging system as in claim 13 wherein the digital data is refreshed at least thirty times per second.

15. An angioscopy imaging system as in claim 12 wherein the digital data provided to the monitor is updated a preselected time interval after a pulsed introduction of flush solution.

16. An angioscopy imaging system as in claim 12 and further including means for detecting the optical density within the vessel such that the digital data provided to the monitor is updated upon detection of a predetermined optical density.

17. An angioscopy imaging system as in claim 12 and further including means for examining the live image contrast obtained during the sequential introduction of flush solution such that the digital data provided to the monitor is updated when the live image contrast decreases from its maximum.

18. An angioscopy imaging system as in claim 9 and further including input means connected to the central processing unit for introducing control commands thereto for controlling the irrigation control signals provided to the irrigation means.

19. An angioscopy imaging system as in claim 18 wherein the irrigation means is responsive to irrigation control signals from the central processing unit to introduce a pulsatile sequence of flush solution to the interior of the vessel.

20. An angioscopy imaging system as in claim 19 wherein the digitizer means is responsive to digitization control signals to update the digital data provided to the monitor in synchronization with the pulsatile introduction of flush solution.

21. An angioscopy imaging system as in claim 20 wherein the digital data provided to the monitor is updated a preselected time interval a pulsed introduction of flush solution.

22. An angioscopy imaging system as in claim 18 wherein the input means includes a keyboard.

23. An angioscopy imaging system as in claim 18 wherein the input means includes a foot pedal.

24. An angioscopy imaging system as in claim 18 wherein the input means includes a handset.

25. An angioscopy imaging system as in claim 9 and further including a second monitor responsive to the electrical output signal to provide the live image.

26. An angioscopy imaging system as in claim 9 and further including a status monitor connected to the central processing unit for displaying information relating to the status of the imaging system.

* * * * *